United States Patent [19]

McAfee

[11] Patent Number: 5,206,377
[45] Date of Patent: Apr. 27, 1993

[54] COMPOUNDS USEFUL AS ANTIPROLIFERATIVE AGENTS

[75] Inventor: Donald A. McAfee, Richmond, Va.

[73] Assignee: Whitby Research, Inc., Richmond, Va.

[21] Appl. No.: 802,723

[22] Filed: Dec. 5, 1991

[51] Int. Cl.$^5$ .................................. C07D 209/10
[52] U.S. Cl. ................. 548/253; 548/506; 548/507
[58] Field of Search ............. 548/506, 507, 253; 514/415, 381

[56] References Cited

FOREIGN PATENT DOCUMENTS 1445516 12/1968 Fed. Rep. of Germany ...... 548/506
3840338  5/1990 Fed. Rep. of Germany ...... 548/507
2186874  8/1987 United Kingdom ............... 548/506

Primary Examiner—C. Warren Ivy
Assistant Examiner—Zinna N. Davis
Attorney, Agent, or Firm—Richard J. Hammond

[57] ABSTRACT

Melatonin compounds are disclosed of the formula

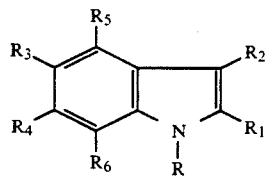

where R is hydrogen or $C_1$ to $C_6$ linear or branched alkylene substituted with phenyl; $R_1$ is hydrogen, substituted benzyl, naphthylmethyl or taken together with $R_2$ and the two carbon atoms of the five-membered hetero ring form the group

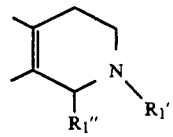

where $R_1'$ is $C_1$ to $C_6$ linear or branched alkanoyl and $R_1''$ is hydrogen, $C_1$ to $C_6$ linear or branched alkyl or phenyl optionally substituted with one or more halogen, amino, nitro, hydroxy, alkyl, alkoxy or haloalkyl; $R_2$ is hydrogen, 1-pyrrolyl, 1-pyrrolyl substituted with one or more alkyl or alkoxy, the group —$(CH_2)_m$—$NHR_2'1$, where m is 1 to 3 and $R_2'$ is phenyl sulfonyl, the phenyl group optionally substituted with alkyl, or —C-(O)—$R_2''$, where $R_2''$ is $C_1$ to $C_6$ linear or branched alkylene substituted with a substituent selected from the group consisting of hydrogen, phenyl, alkoxy, alkoxy substituted with phenyl, carboxylic acid or the alkyl esters thereof, carbamoyloxy alkyl, substituted carbamoyloxy alkyl and amino or 5-(2-alkanoyl) tetrazole; $R_3$, $R_4$, $R_5$ and $R_6$ are the same or different and are $C_1$ to $C_6$ linear or branched alkyl, $C_1$ to $C_6$ linear or branched alkoxy, phenoxy or phenoxy substituted with one or more $C_1$ to $C_6$ linear or branched alkyl.

The compounds display melatonin antagonist and are antiproliferative agents.

8 Claims, 15 Drawing Sheets

COMPOUNDS USEFUL AS ANTIPROLIFERATIVE AGENTS

FIELD OF THE INVENTION

This invention relates to novel 2-aryl substituted tryptamines, carbolines and pyrroles having pharmacological activity, e.g., melatonin antagonist activity and methods for the synthesis thereof.

BACKGROUND OF THE INVENTION

Melatonin, 5-methoxy-N-actyltryptamine, is a major hormone of the pineal gland. The synthesis and secretion of melatonin exhibit a circadian rhythm that changes with the seasons and with age, e.g., pubescence and senescence. The rhythm appears to be the result of both endogenous mechanisms and environmental cues, most notably, the exposure of mammals to light, which inhibits melatonin synthesis and secretion. Melatonin is thought to be the hormonal mediator of photoperiodic changes. Evidence suggests that melatonin is involved in the regulation of circadian rhythms and a variety of neural and endocrine functions. Melatonin has been implicated in a number of human disorders, particularly those relating to chronobiologic abnormalities. Researchers have suggested administering melatonin to alleviate or prevent disturbances in circadian rhythms caused by the rapid crossing of time zones, e.g., jet lag, or changes in work shifts from night to day. See European Patent Application 0 126 630, by Short et al.

Melatonin analogues have been studied for their effects on the reproductive system, specifically antigonadal activity and inhibition of release of luteinizing hormone (LH); see Flaugh et al., *Journal of Medicinal Chemistry*, (1979) 22:63-69.

Frohn et al., *Life Sciences*, Vol. 27, pp. 2043-2046, Pergamon Press, and Clemens et al., *J. Neural Transm.*, (1986) [suppl.] 21:451-459, disclose melatonin analogues wherein the activity of such analogues is related to structure. Analogues with improved metabolic stability, e.g., 2-methyl-6,7-dichloromelatonin, are disclosed.

Heward and Hadley, (1975), *Life Sci.*, 17:1167-1168, reported in-vitro method for measuring the melatonin response of various indoleamines, including melatonin and 5-methoxy-N-acetyltryptamine, by frog skin lightening. Of the compounds disclosed in this article, only N-acetyltryptamine and N-acetylserotonin were reported to have "melatonin blocking activity".

Dubocovich, *Eur. J. Pharmacol.*, 105:193-194, 1984, also reported that N-acetyltryptamine competitively antagonized the inhibitory effect of melatonin in the chicken retina, thus demonstrating melatonin blocking activity by a more sensitive in-vitro method than utilized by Heward and Hadley.

In Cattanoch, et al., *J. Chem Soc.* c(10) 1235-43 (1968) a series of tetrahydro-1H-pyrido [4,3-b] indoles were prepared and examined for their ability to block the pharmacological actions of seratonin. The 2-acetyl derivatives of 8-chloro-2,3,4,5-tetrahydro-1H-pyrido [4,3-b] indole was synthesized but never tested for any type of physiological activity. Also see ibid c(2) 359-66, (1971) for related tetrahydroxyamide [3,4-a] compounds.

Several studies have suggested that the pineal gland may influence the development and growth of mammary tumors in addition to hormone-responsive reproductive tissue. For example, melatonin administration has been shown to inhibit, while pineolectomy generally stimulates mammary carcinogenesis. Melatonin has, in fact, been studied with an aim to prove that it retards hormone responsive breast cancer growth by directly inhibiting all proliferation. See Hill, et al., Cancer Research 40 6121-26, (1988).

It is of continuing interest to identify compounds which can inhibit abnormal cell proliferation, while minimizing side effects.

DESCRIPTION OF THE PREFERRED EMBODIMENT

Figure 1:
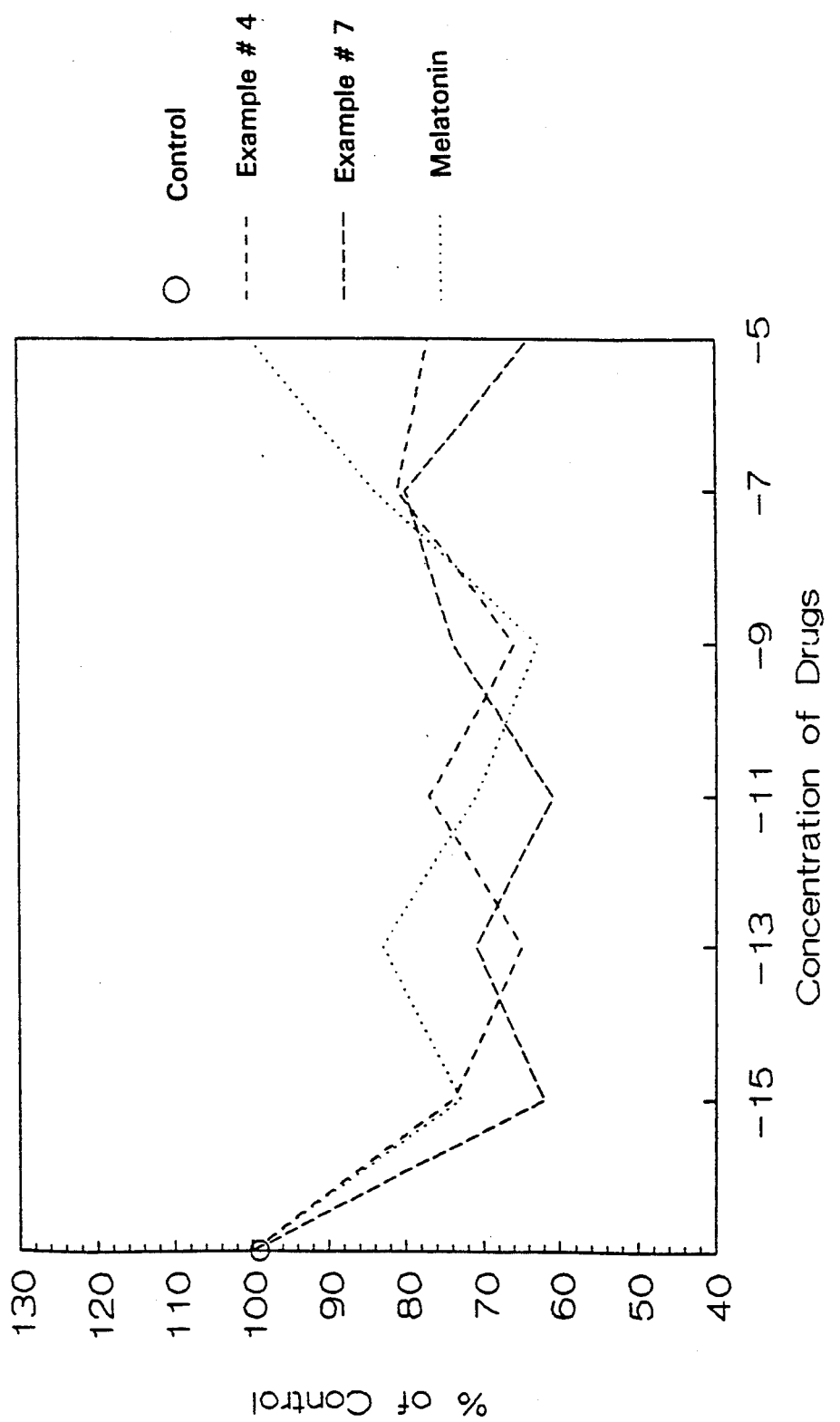
FIGS. 1-6 summarize effects of compounds on cell growth described in Examples 4 and 7, 5 and 3, 2 and 9, 6, 1, as well as 10 and 11.

In the present specification and claims, the following terms apply:

$C_1$ to $C_6$ linear or branched alkyl means straight or branched chain alkyl groups having from 1 to 6 carbon atoms and includes for example, methyl, ethyl, n-propyl, isopropyl, butyl, isobutyl, secondary butyl, tertiary butyl, n-pentyl, isopentyl, neopentyl, n-hexyl, 2-methylpentyl and the like. The term "alkyl" is sometimes used herein to mean $C_1$ to $C_6$ linear or branched alkyl.

Optionally substituted phenyl (or phenyl optionally substituted) means phenyl or phenyl substituted by at least one substituent selected from the group consisting of halogen (or halo), i.e., chloro, bromo, fluoro or iodo, amino, nitro, hydroxy, alkyl, alkoxy which means linear or branched chain alkoxy having 1 to 6 carbon atoms and includes for example, methoxy, ethoxy, propoxy, isopropoxy, butoxy, isobutoxy, secondary butoxy, tertiary butoxy, pentyloxy, isopentyloxy and hexyloxy, haloalkyl which means linear or branched chain alkyl (as defined above) substituted with at least one halogen and includes for example, chloromethyl, chloromethyl, fluoromethyl, 3-fluoropropyl, 4-chlorobutyl, dichloromethyl, difluoromethyl, 2, 2-difluoroethyl, $4_1$ 4-dichlorobutyl, trichloromethyl, trifluoromethyl, 2, 2, 2-trifluoroethyl, 2, 3, 3-trifluoropropyl, 1, 1, 2, 2-tetrafluoroethyl, 2, 2, 3, 3-tetrafluoropropyl and the like. In the case of mono substituents, the phenyl group can be substituted at position 2-, 3- or 4-. Di, tri, tetra and penta substituents are also included. Such substituents may be attached to the phenyl ring at any appropriately available site.

$C_1$ to $C_6$ linear or branched alkylene means branched chain alkylene groups having 1 to 6 carbon atoms and includes for example, the groups methylene, dimethylmethylene, ethylene 2, 2-dimethylpropylene, 2-dimethylbutylene and the like.

$C_1$ to $C_6$ linear or branched alkanoyl means straight or branched chain alkanoyl group having 1 to 6 carbon atoms and includes, for example, acetyl, propinyl, butyryl, isobutyryl, pivaloyl, valeryl, hexanoxyl and the like.

Carbamoyloxyalkyl means that the single substituent on the nitrogen atom (attached to alkylene group) of the carbamoyl moiety is selected from the group consisting of hydrogen, linear or branched chain alkyl group having 1 to 6 carbon atoms, phenylalkyl which means the alkyl moiety has 1 to 6 liner or branched chain carbon atoms and includes for example, benzyl, 2-phenylethyl, 1-phenylethyl, 3-phenylpropyl, 4-phenylbutyl, 6- phenylhexyl and the like and substituted phenylalkyl which means the above-mentioned phenylalkyl substituted by at least one substituent selected from the group consisting of halo, amino, nitro, hydroxy, alkyl, alkoxy and haloalkyl on the phenyl nucleus and includes for example, N-methyl carbamoyloxymethyl, N-ethyl carbamoyloxymethyl, N-propyl carbamoyloxymethyl, N-butyl carbamoyloxymethyl, 1-(N-methylcarbamoyloxy) ethyl and 2-(N-ethylcarbamoyloxy) ethyl.

Substituted carbamoyloxy alkyl means the above described N-substituted carbamoyloxy alkyl moieties bearing substituents on the alkyl group (the group attached to the oxygen atom of the carbamoyloxy moiety) and includes phenyl or optionally substituted phenyl and such as the groups (N-methyl carbamoyloxy)-phenylmethyl, N-ethyl carbamoyloxymethylphenyl, N-propyl carbamoyloxymethylphenyl, N-butyl carbamoyloxymethylphenyl, 2-(N-methyl carbamoyloxy)-2-phenylethyl, 2-(N-ethyl carbamoyloxy)-2-phenylethyl, 3-(N-methyl carbamoyloxy)-3-phenylpropyl, 4-(N-methyl carbamoyloxy)-4-phenylpropyl and the like.

The compounds of the present invention are those represented by the formula

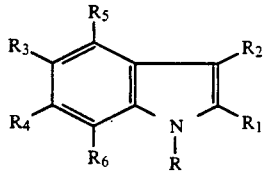

where R is hydrogen or $C_1$ to $C_6$ linear or branched alkylene substituted with phenyl;

$R_1$ is hydrogen, substituted benzyl, naphthylmethyl or taken together with $R_2$ and the two carbon atoms of the five-membered hetero ring form the group

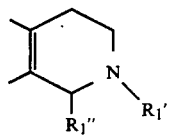

where $R_1'$ is $C_1$ to $C_6$ linear or branched alkanoyl and $R_1''$ is hydrogen, $C_1$ to $C_6$ linear or branched alkyl or phenyl optionally substituted with one or more halogen, amino, nitro, hydroxy, alkyl, alkoxy or haloalkyl;

$R_2$ is hydrogen, 1-pyrrolyl, 1-pyrrolyl substituted with one or more alkyl or alkoxy, the group —$(CH_2)_m NHR_2'$ where m is 1 to 3 and $R_2'$ is phenyl sulfonyl, the phenyl group optionally substituted with alkyl, or —C(O)—$R_2''$, where $R_2''$ is $C_1$ to $C_6$ liner or branched alkylene substituted with a substituent selected from the group consisting of hydrogen, phenyl, alkoxy, alkoxy substituted with phenyl, carboxylic acid or the alkyl esters thereof, carbamoyloxy alkyl, substituted carbamoyloxy alkyl and amino or 5-(2-alkanoyl) tetrazole;

$R_3$, $R_4$, $R_5$ and $R_6$ are the same or different and are hydrogen $C_1$ to $C_6$ linear or branched alkyl, $C_1$ to $C_6$ linear or branched alkoxy, phenoxy or phenoxy substituted with one or more $C_1$ to $C_6$ linear or branched alkyl;

Compounds of the formula

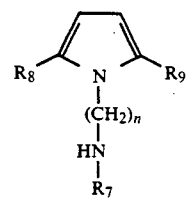

where $R_7$ is $C_1$ to $C_6$ linear or branched alkanoyl, $R_8$ and $R_9$ are the same or different and are $C_1$ to $C_6$ linear or branched alkyl, and n is 1 to 3.

In the compounds of formula I, it is preferred that $R_1$ and $R_2$ are taken together with two carbon atoms of the hetero form compounds of the formula

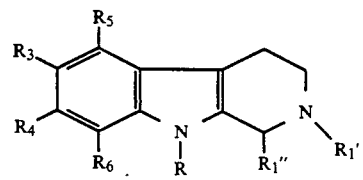

In the preferred compounds of formula IA it is most preferred that R, $R_4$, $R_5$, $R_6$ and $R_1''$ are hydrogen and $R_3$ is halo, $C_1$ to $C_6$ linear or branched alkoxy or phenyoxy.

Especially preferred in the compounds of formula IA are those where $R_3$ is bromo, methoxy, phenoxy and $R_1'$ is acetyl.

Another preferred group of compounds of formula I are those of the formula where $R_1$, $R_3$, $R_4$, $R_5$, $R_6$ are hydrogen and $R_2$ is 5-(alkanoyl) tetrazole.

Especially preferred for such compounds are those where R is hydrogen or benzyl and $R_2$ is 5(2-acetyl).

A further preferred group of compounds of formula I are those where $R_2$ is phenylsulfonyl and R, $R_1$, $R_3$, $R_4$, $R_5$ and $R_6$ are hydrogen. The phenyl may be unsubstituted or substituted with one or more $C_1$ to $C_6$ linear or branched alkyl or 1-pyrrolyl which may be unsubstituted or substituted with one or more $C_1$ to $C_6$ linear or branched alkyl. $R_2$ can also be the group —$(CH_2)_m$—$NHR'_2$ where m is an integer from 1 to 3 and R' is the group —C(O)—$R_2''$ where $R_2''$ is $C_1$ to $C_6$ linear or branched alkylene substituted with a substituent selected from the groups consisting of phenyl or $C_1$ to $C_6$ linear or branched alkoxy. The alkoxy group can be unsubstituted or substituted with phenyl, carbamoyloxy alkyl or amino.

Particularly preferred for the above preferred compounds are those where $R_2$ is (4-methyl) phenyl sulfonyl, 1-(2, 5-dimethyl) pyrrolyl or the group —$(CH_2)_m$—$NHR_2'$ where $R_2'$ is —C(O)—$R_2''$ where $R_2''$ is $C_1$ to $C_6$ linear or branched alkylene substituted with phenyl or with $C_1$ to $C_6$ linear or branched alkoxy and m is as previously defined. The alkoxy group can be unsubstituted or substituted with phenyl.

Especially preferred are the compounds where $R_2''$ is $C_1$ to $C_6$ linear or branched ethyl, 2-(N-benzyl carbamoyloxy) ethyl, 3-(N-methyl carbamoyloxy) propyl, 4-(N-methyl carbamoyloxy) butyl and the like.

In the compounds of formula II, it is preferred that $R_7$ is acetyl. Particularly preferred of the preferred compounds are those where $R_8$ and $R_9$ are the same and are acetyl.

In preparing the compounds of formula IA a substituted tryptamine, e.g.,

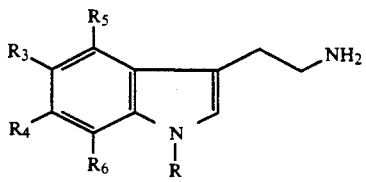

where R, $R_3$, $R_4$, $R_5$ and $R_6$ are as previously defined is treated with an aldehyde of the formula $R_1''CHO$ to produce the carboline intermediate. Acylation provides the compounds of formula IA.

In preparing the compounds of formula I where $R_2$ is the group $-(CH_2)_m-NHR_2'$, the compounds of formula IA are first hydrogenated to open the 6-membered, nitrogen containing ring (the tetrahydropyridyl ring). Acylation provides the desired product. Other compounds of formula I can be prepared by using various substituted tryptamines as starting materials. These starting compounds are not new and their preparation is well known to those skilled in the art.

The compounds of formula II can be readily prepared by the reaction of a diaminoalkane, e.g., ethylenediamine, with a diketoalkane such as acetyl acetone. The resulting 2,5-dialkyl pyrrole bearing an alkylamino group can then be subjected to acylation to provide the desired compounds of formula II.

Specific preferred compounds which are within the scope of this invention include:
1-N-Acetyl-3-(3,5-dimethyl-1H-pyrrolyl)ethylamine
N-Benzyloxyoarbonyltryptamine
2-Benzyl-3-ethylaoetamido-5-methoxyindole
2-Benzyl-N-propionyltryptamine
1-Methyl-2-N-acetyl-6-benzyloxy-1,2,3,4-tetrahydro-β-carboline
1-Methyl-2-N-acetyl-6-methoxy-1,2,3,4-tetrahydro-β-carboline
1-N-propionyl-3-(3,5-dimethyl-1H-pryyolyl)ethylamine
2-Benzyl-N-acetyltryptamine
2-(1-Naphthylmethyl)-N-acetyltryptamine
2-(4-Methylphenyl)methyl-N-acetyltryptamine
1-Propyl-2-N-acetyl-6-methoxy-1,2,3,4-tetrahydro-β-carboline
1-Methyl-2-N-acetyl-1,2,3,4-tetrahydro-β-carboline
1-Methyl-2-N-propionyl-6-methoxy-1,2,3,4-tetrahydro-β-carboline
1-Methyl-2-N-acetyl-6-benzyloxy-1,2,3,4-tetrahydro-β-carboline
2-N-acetyl-1,2,3,4-tetrahydro-β-carboline
1-Phenyl-2-N-acetyl-5-bromo-1,2,3,4-tetrahydro-β-carboline
2-N-Acetyl-5-bromo-1,2,3,4-tetrahydro-β-carboline
2-(4-Methoxyphenyl)methyl-3-(N-propionyl)aminoethylindole
2-(4-Tolylmethyl)-3-ethylacetamidoindole
2-(4-Methoxyphenyl)methyl-3-ethylacetamidoindole The above compounds may be made as described in the examples below.

A preferred embodiment of the present invention comprises a method of treating any disorder in which it is therapeutic to mimic or inhibit melatonin function that inhibits tumorigenesis by administering a therapeutically effective amount of one or more of the compounds of the present invention to a patient suffering from such disorder.

Another preferred embodiment of the present invention comprises a method of inhibiting or reducing the growth of cancerous tumor cells by administering (e.g., injection, oral, topical) a therapeutically-effective amount of one or more of the compounds of the present invention to a patient suffering from such disorder.

Another preferred embodiment of the present invention comprises a method of treating various cell proliferation disorders related to altered melatonin function or influenced by melatonin by administering a therapeutically-effective amount of one or more of the compounds of the present invention to a patient suffering from one or more of such disorders.

Another preferred embodiment of the present invention comprises a method of treating or inducing various endocrine-related conditions attributed to altered melatonin function or influenced by melatonin particularly relating to mammary carcinogenous and the reproductive maturation and function, e.g., idiopathic delayed puberty, premature labor, and antifertility, by administering a therapeutically-effective amount of one or more of the compounds of the present invention to a patient suffering from such endocrine related conditions. In addition, it is thought that the melatonin agonist compounds of the invention can be used to treat or prevent glaucoma by lowering the intraocular pressure and to manipulate body weight by administering an effective amount of one or more of the melatonin agonist compounds herein.

In general, a pharmacologically effective daily dose can be from 0.01 mg/kg to 25 mg/kg per day, bearing in mind, of course, that in selecting the appropriate dosage in any specific case, consideration must be given to the patient's weight, general health, metabolism, age and other factors which influence response to the drug. A particularly preferred dose is 1.0 mg/kg per day.

Another embodiment of this invention is the provision of pharmaceutical compositions in dosage unit form which comprise from about 2 mg. to 500 mg. of a compound of the above formula.

The pharmaceutical composition may be in a form suitable for oral use, for example, as tablets, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents, and preserving agents in order to provide a pharmaceutically elegant and palatable preparation. Tablets contain the active ingredient in admixture with non-toxic pharmaceutically acceptable excipients which are suitable for manufacture of tablets.

These excipients may be, for example, inert diluents, for example calcium carbonate, sodium carbonate, lactose, calcium phosphate, or sodium phosphate; granulating disintegrating agents, for example maize starch, or alginic acid; binding agent, for example starch, gelatine, or acacia; and lubricating agents, for example magnesium stearate, stearic acids, or talc. The tablets may be uncoated or they may be coated by known techniques to delay disintegration and adsorption in the gastrointestinal tract. Thereby a sustained action over a longer period can be provided.

Formulations for oral use can also be presented as hard gelatine capsules wherein the active ingredient is mixed with an inert solid diluent, for example calcium carbonate, calcium phosphate, or kaolin, or as soft gelatine capsules wherein the active ingredient is mixed with an oil medkiu, for example arachis oil, liquid paraffin, or olive oil.

Aqueous suspensions contain the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth, and gum acacia; dispersing or wetting agents can be a naturally-occurring phosphatide, for example lecithin, or condensation products of an alkylene oxide with fatty acids, for example of polyoxethylene stearate, or condensation products of ethylene oxide with long chain aliphatic alcohols, for example heptadecaethyleneoxycetanol, or condensation products of ethylene oxide with partial esters derived from fatty acids and a hexitol, for example, polyoxyethylene sorbitol monooleate, or condensation product of ethylene oxide with partial esters derived from fatty acids and hexitol anhydrides, for example polyoxyethylene sorbitan monooleate. The said aqueous suspensions can also contain one or more preservatives, for example ethyl, n-propyl, or p-hydroxy benzoate, one or more coloring agents, one or more flavoring agents, and one or more sweetening agents, such as sucrose, saccharin, or sodium or calcium cyclamate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents, can also be present.

Syrups and elixirs can be formulated with sweetening agents, for example glycerol, sorbitol or sucrose. Such formulation can also contain a demulcent, a preservative and flavoring and coloring agents. The pharmaceutical compositions can be in the form of a sterile injectable preparation, for example, as a sterile injectable aqueous suspension. This suspension can be formulated according to the known art using those suitable dispersing or wetting agents and suspending agents which have been mentioned above. The sterile injectable preparation can also be a sterile injectable solution or suspension in a non-toxic parenterally-acceptable diluent or solvent, for example, as a solution in 1,3-butane diol.

The pharmaceutical compositions of the present invention also include compositions for transdermal and/or intranasal administration. Thus, the compounds of the present invention can be compounded with a penetration-enhancing agent such as 1-n-dodecylazacyclopentan-2-one or the other penetration-enhancing agents disclosed in U.S. Pat. Nos. 3,991,203 and 4,122,170 Which are hereby incorporated by reference to describe penetration-enhancing agents which can be included in the transdermal or intranasal compositions of this invention.

The pharmaceutical compositions can be tableted or otherwise formulated so that for every 100 parts by weight of the composition there are present between 5 and 95 parts by weight of the active ingredient. The dosage unit form will generally contain between about 1 mg. and about 100 mg. of the active ingredient of the formula stated above.

From the foregoing formulation discussion it is apparent that the compositions of this invention can be administered orally or parenterally. The term parenteral as used herein includes subcutaneous injection, intravenous, intramuscular, or intrasternal injection or infusion techniques.

To illustrate the manner in which the invention can be carried out, the following examples are given. It is understood, however, that the examples are for the purpose of illustration and the invention is not to be regarded as limited to any of the specific materials or conditions therein.

EXAMPLE 1

PREPARATION OF
1-N-ACETYL-3-(3,5-DIMETHYL-1H-PYRROLYL)ETHYLAMINE

To a stirred solution of 0.50 g (.083 mol) of ethylene diamine and 9.49 g (.083 mol) of acetonyl acetone in 200 mLs toluene was added five drops of acetic acid. The mixture was brought to reflux overnight under a Dean-Stark trap and after workup yielded the product which showed characteristic peaks: NMR (300 MHz, CDCl$_3$) δ 3.85 (t, 2H), 2.95 (t, 2H), 2.25 (s, 6H).

To 1.0 g (7.2 mmol) of the above product and 3.0 mL (0.022 mol) triethylamine in toluene (0° C.) was added 0.57 g (7.2 mmol) acetyl chloride and the mixture was stirred at RT for 20 min. After workup and purification by flash chromatography (Silica, 8:2 EtOAc:pet. ether) the product was isolated and showed characteristic peaks: NMR (300 MHz, CDCl$_3$) δ 3.9 (t, 2H), 3.45 (m, 2H), 2.2 (s, 6H), 2.0 (s 3H).

Anal. calc. for C$_{10}$H$_{16}$N$_2$O: C, 66.64; H, 8.95; N, 15.54. Observed : C, 66.82; H, 9.02; N, 15.63.

EXAMPLE 2

PREPARATION OF
N-BENZYLOXYCARBONYLTRYPTAMINE

To a mixture of tryptamine 1.0 g (6.2 mmol) in a mixture of CHCl$_3$ and H$_2$O, was added 1.1 g (6.2 mmol) benzylchloroformate, followed by dropwise addition of sat. NaHCO$_3$ solution to maintain alkaline conditions. The reaction was stirred for 2 hrs. The reaction was extracted with CHCl$_3$ and the organic layer was concentrated to dryness giving a dark yellow oil. The oil was crystallized from ethanol/water to give an off-white crystalline product.

Anal. calc. for C$_{18}$H$_{18}$N$_2$O$_2$: C, 73.0 ; H, 6.1; N, 10.0. Observed : C, 73.31; H, 6.05; N, 9.72.

EXAMPLE 3

PREPARATION OF
1=METHYL-2-N-ACETYL-6=METHOXY-1,2,3,4-TETRAHYDRO-δ-CARBOLINE

To a suspension of 3.0 g (15.8 mmol) 5-methoxytryptamine in water was added concentrated HC$_1$ dropwise until a solution was obtained, giving a pH of 3.0. Then 8.0 mL acetaldehyde was added and the reaction placed in an oil bath at 85° C. and stirred for 1.25 hrs. The reaction was cooled to room temperature, acidified with concentrated HC$_1$ to pH 1, and concentrated in vacuo to give an orange brown solid, which was dissolved in water and made basic with NH$_4$OH. After extraction with CH$_2$Cl$_2$, the organic layer was dried over MgSO$_4$, filtered and concentrated in vacuo to give an off-white solid, which showed characteristic peaks: NMR (CDCl$_3$): δ: 1.45 ppm (d, 3H), 3.85 ppm (s, 3H).

To a solution of 700 mg (3.24 mmol) 1-methyl-6-methoxy-1,2,3,4-tetrahydro-β-carboline, and .5 drops NO$_4$OH in ethyl acetate was added 0.4 mL (3.88 mmol) acetic anhydride under N$_2$ gas. The reaction was stirred for 20 min. and then washed with water. The organic layer collected was dried over MgSO$_4$, filtered, and concentrated in vacuo to a dark oil. The oil was dissolved in methanol and chromatographed on reverse phase C-18 using methanol and water. The product was collected and concentrated to a white solid, which showed characteristic peaks: NMR (CDCl$_3$) δ: 1.45 ppm (d, 3H), 2.25 ppm (s, 3H), 3.85 ppm (s, 3H).

Anal. calc. for $C_{15}H_{19}N_2O_2$: C, 69.47; H, 7.38; N, 10.80. Observed: C, 69.21; H, 7.12; N, 10.93.

EXAMPLE 4

PREPARATION OF 2-BENZYL-3-ETHYLACETAMIDO-5-METHOXYINDOLE

To a solution of 3.05 g (0.0288 mol) of benzaldehyde in 250 mL toluene was added 5.0 g (0.0261 mol) of 5-methoxytryptamine. The solution was refluxed for 16 hours with removal of water by a Dean-Stark trap. The mixture was allowed to cool and 3 mL of conc. HC$_1$ was added and the reaction refluxed for an additional 1 hour until all the water was removed. The reaction was then cooled and the product filtered off and washed with cold EtOAC and cold pet. ether. The product was dissolved in water and adjusted to pH 10 with conc. NO$_4$OH and extracted into CH$_2$Cl$_2$. The solvent was removed under reduced pressure to give a yellow oil which was purified by flash chromatography on Silica (50:50 EtOAc:pet ether to 100% EtOAc) giving 3.0 of product (41%) as a ale-yellow solid.

Into a Parr high pressure reactor were placed 3.0 g of the above product, 15 mL of glacial acetic acid, 90 mL of deionized water, 10 mL of methanol and 0.5 g of 10% Pd/C. The apparatus was assembled and flushed 3× with hydrogen, then placed under 110 psi hydrogen and heated to 35° C. with stirring for 4 hours. The reaction was filtered and made basic (pH 10) with conc. NO$_4$OH and extracted with CH$_2$Cl$_2$ (3×). The solvent was dried (MgSO$_4$), filtered, and removed under reduced pressure to give 2.76 g of a colorless oil (91%).

Dissolved in 50 mL of EtOAc was 0.25 g of 2-benzyl-5-methoxytryptamine (0.9 mmol) and 3 drops of conc. NO$_4$OH. Then 0.25 mL of acetic anhydride was added and the reaction was stirred for 15 minutes under nitrogen. The reaction was washed with water (3×), washed once with sat. NaCl solution, dried (MgSO$_4$), filtered, and evaporated under reduced pressure leaving an orange oil, which was purified on HPLC: reverse phase, solvent 55% MeOH→60% MeOH gradient curve, flow=8 mL/min. The compound was collected, methanol removed under reduced pressure and the water removed, leaving 0.2 g of a pale yellow solid (69%), which showed characteristic peaks: NMR (CDCl$_3$) δ: .1.8 (s 3H), 3.9 (s, 3H), 4.1 (s, 2H).

EXAMPLE 5

RATION OF 2-BENZYL-N-PROPIONYLTRYPTAMINE

To 2.3 g (9.2 mmol) of 2-benzyltryptamine in ethyl acetate was added 5 drops NO$_4$OH and excess K$_2$CO$_3$. The mixture was stirred under N$_2$ and 1.8 g (13.8 mmol) propionic anhydride was added. The reaction was washed with sat. NaC$_1$ soln. then H$_2$O. The organic layer was dried over MgSO$_4$, filtered, and concentrated in vacuo to give a brown oil. The oil was purified by reverse phase chromatography using methanol/water, giving a white solid showing characteristic peaks: NMR (CDCl$_3$) δ: 1.0 ppm (t, 3H, 2.3 (q, 2H), 4.0 (s, 2H). mp. 100°–201° C.

EXAMPLE 6

PREPARATION OF 2-N-ACETYL-1,2,3,4-TETRAHYDRO-β-CARBOLINE

To a solution of 3.2 g (20 mmol) tryptamine in 20 ml 1N hydrochloric acid was added 2.2g (24 mmol) glyoxylic acid monohydrate in 70 ml water. This solution was stirred for 1 hour at reflux, cooled, rendered strongly basic with concentrated ammonium hydroxide, whereupon an oily residue appeared. Continuous stirring resulted in solidification of this crude product, which was crystallized from ethanol/water. Drying gave a solid with a melting point of 206°–209° C. This product was acetylated analogous to the procedure used in Example 3 to give an off-white solid product with a melting point of 240°–241° C.

Anal. calc. for $C_{13}H_{14}N_2O$: C, 72.87; H, 6.59; N,13.07. Observed : C, 72 68; H, 6.65; N, 12.95.

EXAMPLE 7

PREPARATION OF 1-METHYL-2-N-ACETYL-6-BENZYLOXY-1,2,3,4-TETRAHYDRO-β-CARBOLINE

The procedure of the first step Example 3 was used, substituting 5-benzyloxytryptamine for 5-methoxytryptamine. This resultant material was acetylated employing the same procedure as in the second step of example 3, and the resultant product crystallized from ethyl acetate. The product showed characteristic peaks: NMR (CDCl$_3$): δ: 1.45 (d, H), 5.1 (s, H).

Anal. calc. for $C_{21}H_{23}N_2O_2$: C, 75.20; H, 6.91; N, 8.35. Observed : C, 75.32; H, 6.74; N, 8.52.

EXAMPLE 8

PREPARATION OF 2-BENZYL-3-ETHYLACETAMIDOINDOLE

The procedure of Example 4 was used, substituting tryptamine for 5-methoxytryptamine. NMR (CDCl$_3$): δ: 1.7 (s, H), 2.9 (t, 2H), 3.4 (dd, 2H), 4.0 (s, 2H), 5.6 (s, 1H), 7.0–7.3 (m, 8H), 7.5 (d, H), 8.4 (s, 1H).

Anal. calc. for $C_{21}H_{23}N_2O_2$ (0.5 mole H$_2$O) : C, 75.72; H, 7.02; N, 9.29. Observed : C, 75.58; H, 6.88; N, 9.08.

EXAMPLE 9

PREPARATION OF 2-(1-NAPHTHYLMETHYL)-3-ETHYLACETAMIDOINDOLE

The procedure of Example 4 was used, substituting 1-naphthaldehyde for benzaldehyde and tryptamine for 5-methoxytryptamine.

EXAMPLE 10

PREPARATION OF 2-(4-TOLYLMETHYL)-3-ETHYLACETAMIDOINDOLE

The procedure of Example 4 was used, substituting p-tolualdehyde for benzaldehyde and tryptamine for 5-methoxytryptamine.

EXAMPLE 11

PREPARATION OF 2-(4-METHOXYPHENYL)METHYL-3-ETHYLACETAMIDOINDOLE

The procedure of Example 4 was used, substituting p-anisaldehyde for benzaldehyde and tryptamine for 5-methoxytryptamine.

EXAMPLE 12

The above examples were tested for their ability to inhibit the growth of both estrogen positive (MCF-7) and estrogen negative (Hs0578t) human breast cancer cell lines in culture. The antiproliferative effects of these compounds were compared with melatonin, a reference molecule known to inhibit growth of estrogen positive cell lines, and, at high concentrations, can inhibit estrogen negative cell lines such as Hs0578t.

MCF-7 cells were maintained in Dulbecco's modified Eagle's medium (DMEM), supplemented with 10% fetal bovine serum (FBS), penicillin (10,000 units/ml) and streptomycin (10 mg/ml) at 37° C in a humidified atmosphere containing 5% $CO_2$. Hs0578t cells were maintained under similar conditions, however DMEM containing high glucose was used and 10 ug/ml of insulin was added to the medium.

Prior to each experiment, cells from stock flasks were suspended by treatment with 0.2% EDTA in phosphate buffered saline (pH 7.3). The cells were then centrifuged at 1000 rpm for 7 minutes, then resuspended in fresh medium and counted on a hemocytometer. Cells were adjusted to a density of $3.0 \times 10^6$/plate in 5 mls of supplemented plating medium. After 5 hours, the plating medium was replaced with fresh medium containing either melatonin or the above examples in concentrations ranging from $10^{-15}M$ to $10^{-15}M$. These compounds were initially dissolved in ethanol and diluted to the appropriate final concentration with DMEM; the final concentration of ethanol per plate was 0.005%. Control cells were exposed to the ethanol vehicle alone (0.005%). Five days after initial seeding, the cells were resuspended with PBS-EDTA and counted on a hemocytometer to determine the total cell counts per plate.

Each experiment was run using triplicate plates for each concentration of melatonin or above example as well as the vehicle controls. Cell growth in each of the experimental plates was expressed as a percent of control growth (100%). A given concentration of either an above example or of melatonin was considered to be inhibitory if it decreased cell proliferation by 20% or more as compared with controls. Since most of the dose-response curves were irregular, the approximate $IC_{50}$ for each example was estimated from a best fit (manually fitted) curve spanning from the 100% control growth level to the maximal inhibitory concentration of that example.

Effects of the above examples on estrogen receptor positive and estrogen receptor negative human breast cancer cell lines (MCF-7 and Hs0578t, respectively) are summarized in FIGS. 1–15, and discussed below. FIGS. 1–6 summarize effects on the MCF-7 cell line, while FIGS. 7–15 describe effects on the Hs0578t cell line.

In FIG. 1, it can be seen that Examples #4 and 7 cause an inhibition of MCF-7 cell growth. Example #4 shows an $IC_{50}$ of about $6 \times 10^{-16}M$ as compared with an $IC_{50}$ of $1 \times 10^{-14}M$ for melatonin, making this example 60 times more potent than melatonin. All concentrations of Example #4 were inhibitory to cell growth. The maximal inhibitory effect of Example #4 was 35% at $10^{-13}M$ Example #7 has an $_{50}$ of $1 \times 10^{-16}M$, making this 100 times more potent than melatonin. All concentrations of Example #7 were inhibitory, with the maximal effect of 37% inhibition seen at $10^{-15}M$.

Figure 2:
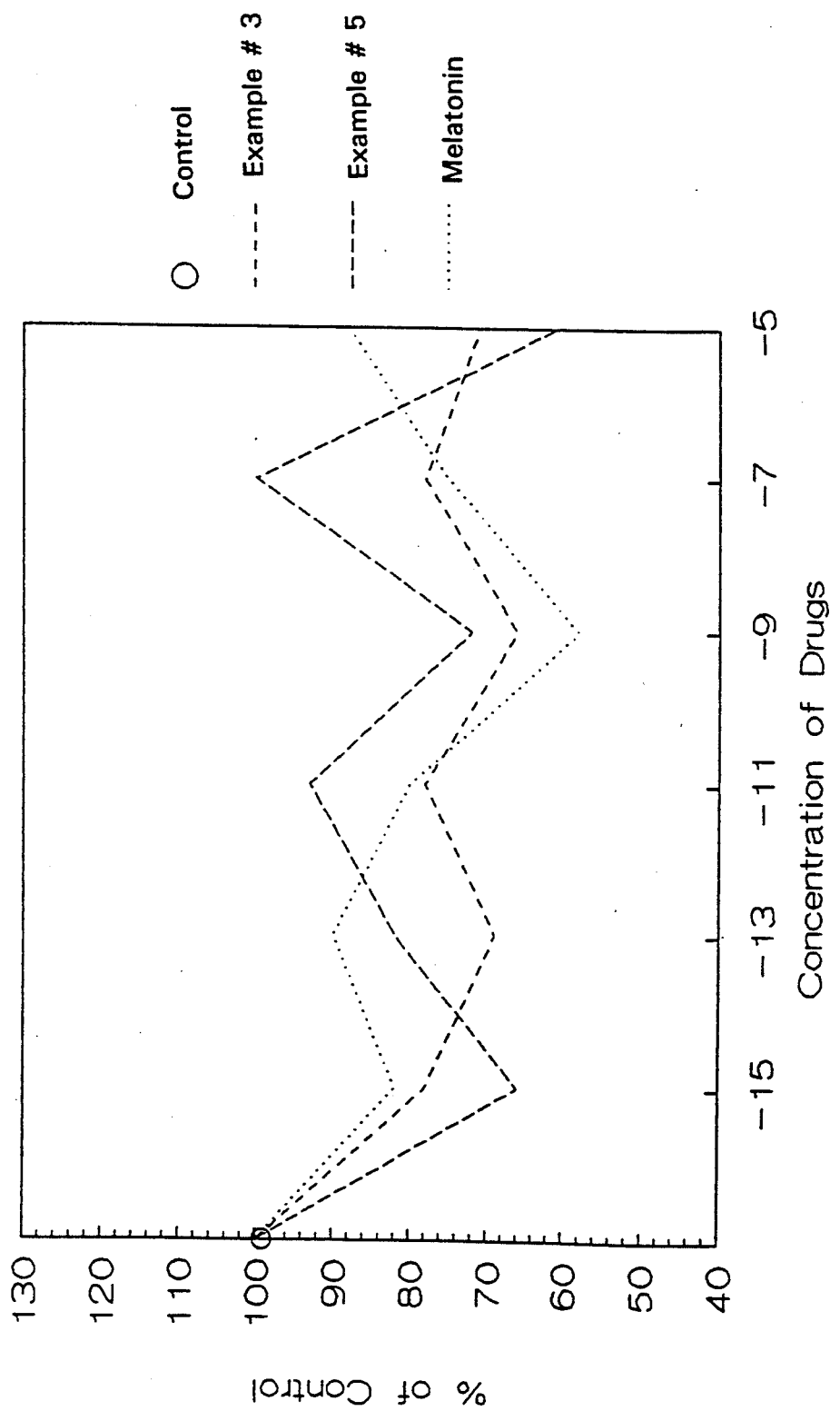

In FIG. 2, Example #3 inhibited MCF-7 cell growth at all concentrations, while Example #5 inhibited cell growth at all concentrations except $10^{-13}M$, $10^{-11}M$ and $10^{-7}M$ Example #3 has an $IC_{50}$ of about $8 \times 10^{-15}M$. The $IC_{50}$ for Example #5 could not be calculated due to the highly irregular nature of the dose-response curve, however the maximal effect was seen at $10^{-5}M$.

Figure 3:
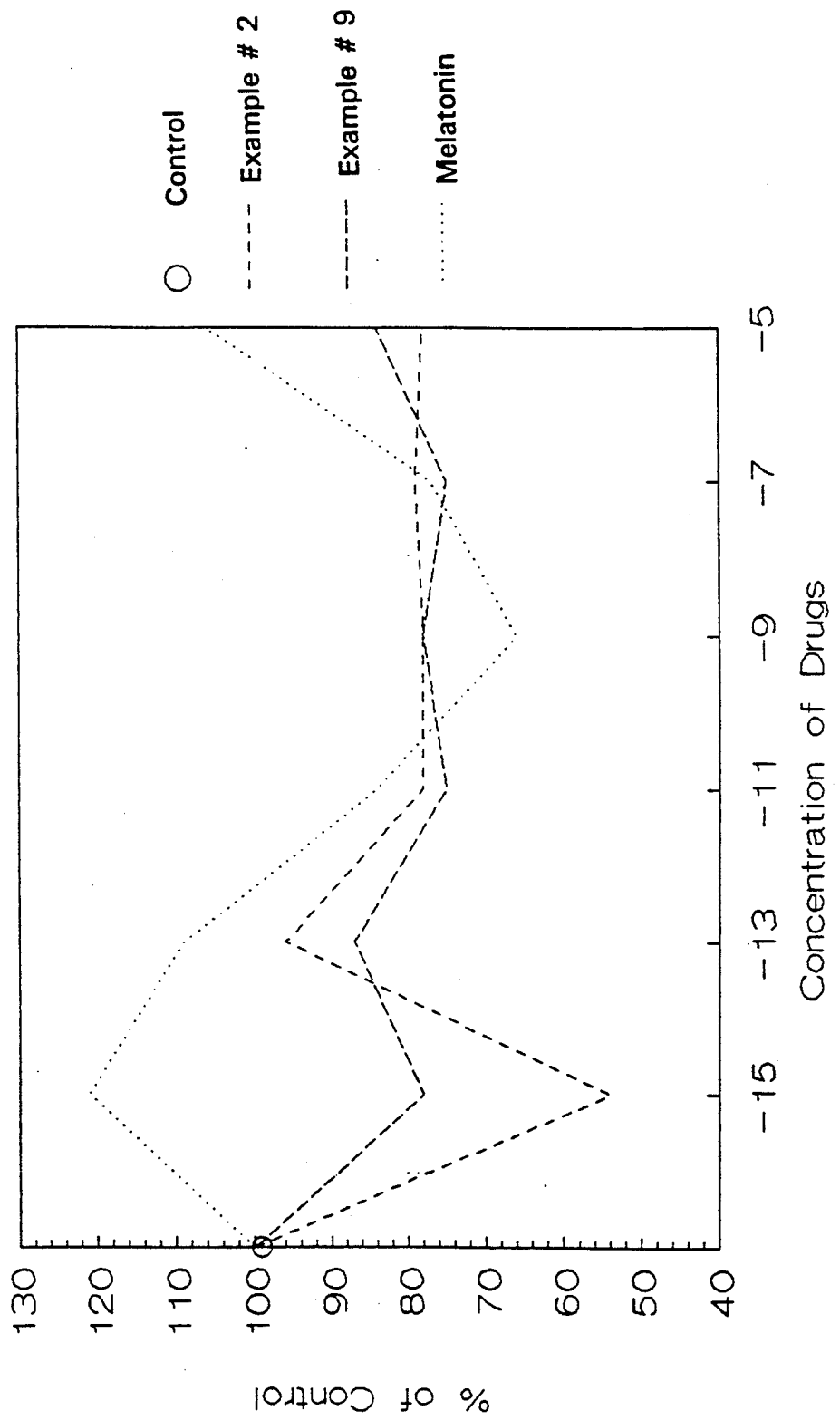

FIG. 3 shows inhibition of MCF-7 cell growth at al concentrations for Examples #2 and 9, with the exceptions of Example #2 at $10^{-13}M$ and Example #9 at $10^{-13}M$ and $10^{-5}M$. Both Example #2 and Example #9 show IC50's of approximately $1 \times 10^{-16}M$.

Figure 4:
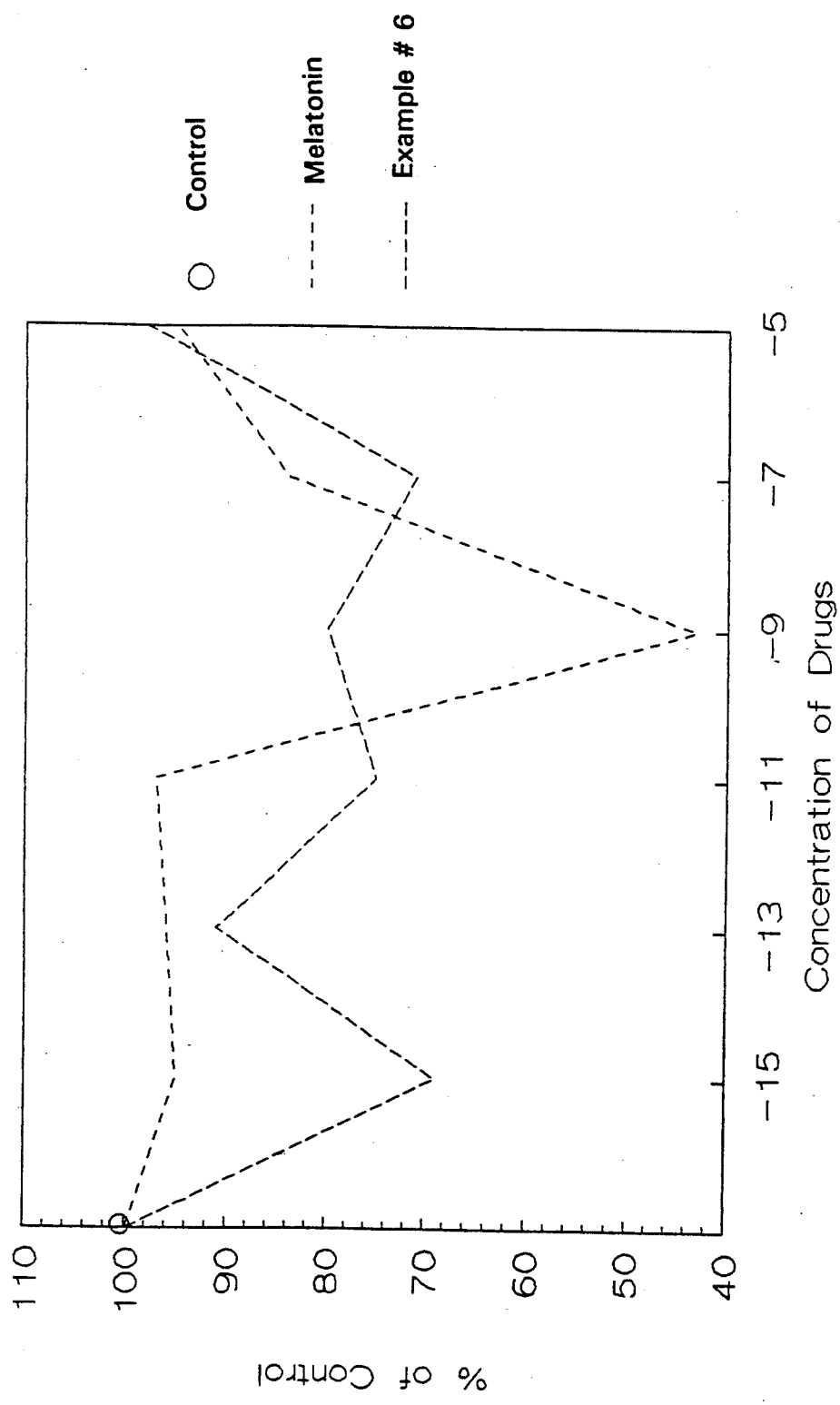

FIG. 4 shows an $IC_{50}$ of approximately $1 \times 10^{-16}M$ for Example #6. All concentrations except $10^{-13}M$ and $10^{-5}M$ were inhibitory to MCF-7 cell growth.

Figure 5:
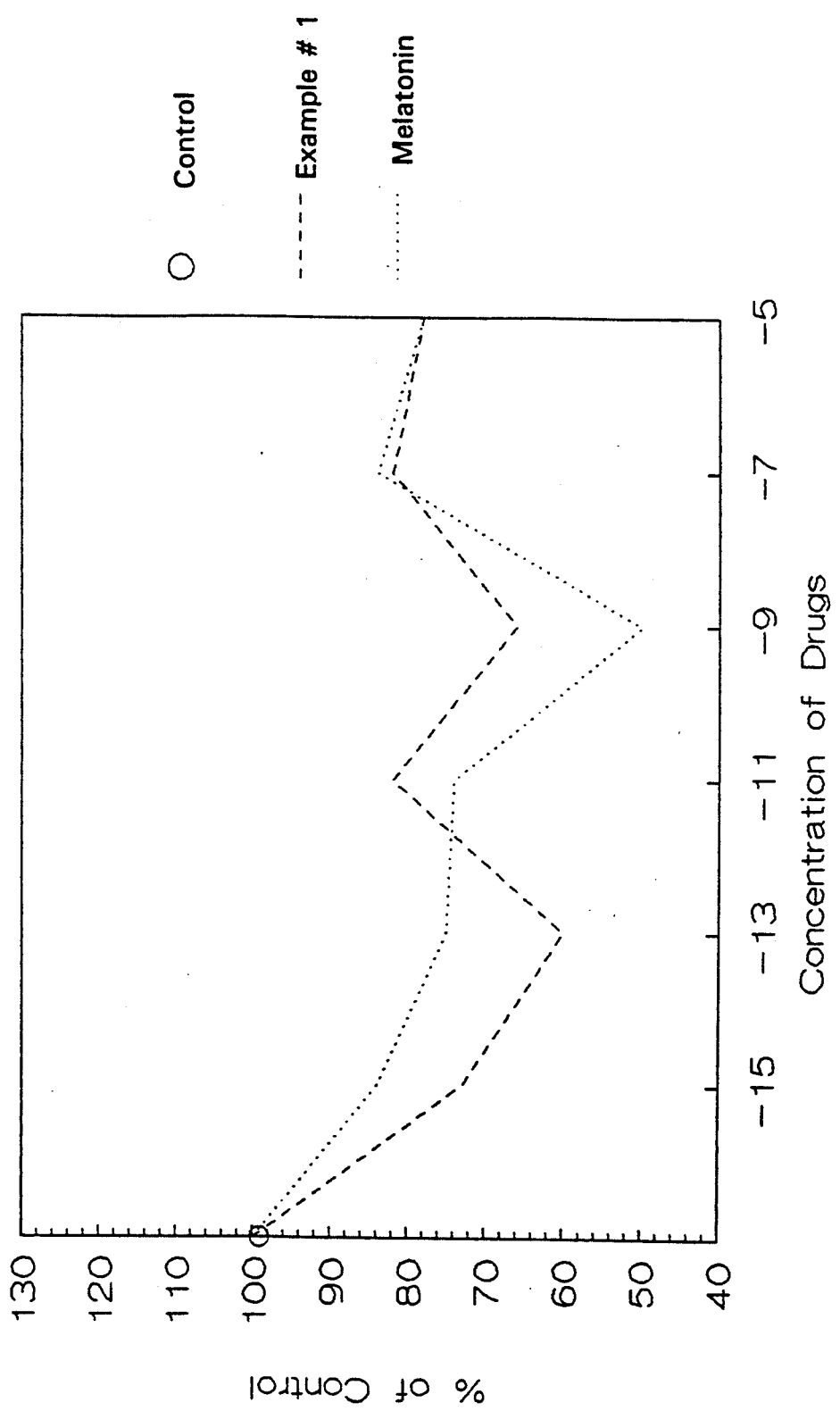

FIG. 5 shows that Example #1 all concentrations except $10^{-11}M$ and $10^{-7}M$ inhibited MCF-7 cell growth, with an $IC_{50}$ of $4 \times 10^{=16}M$.

Figure 6:
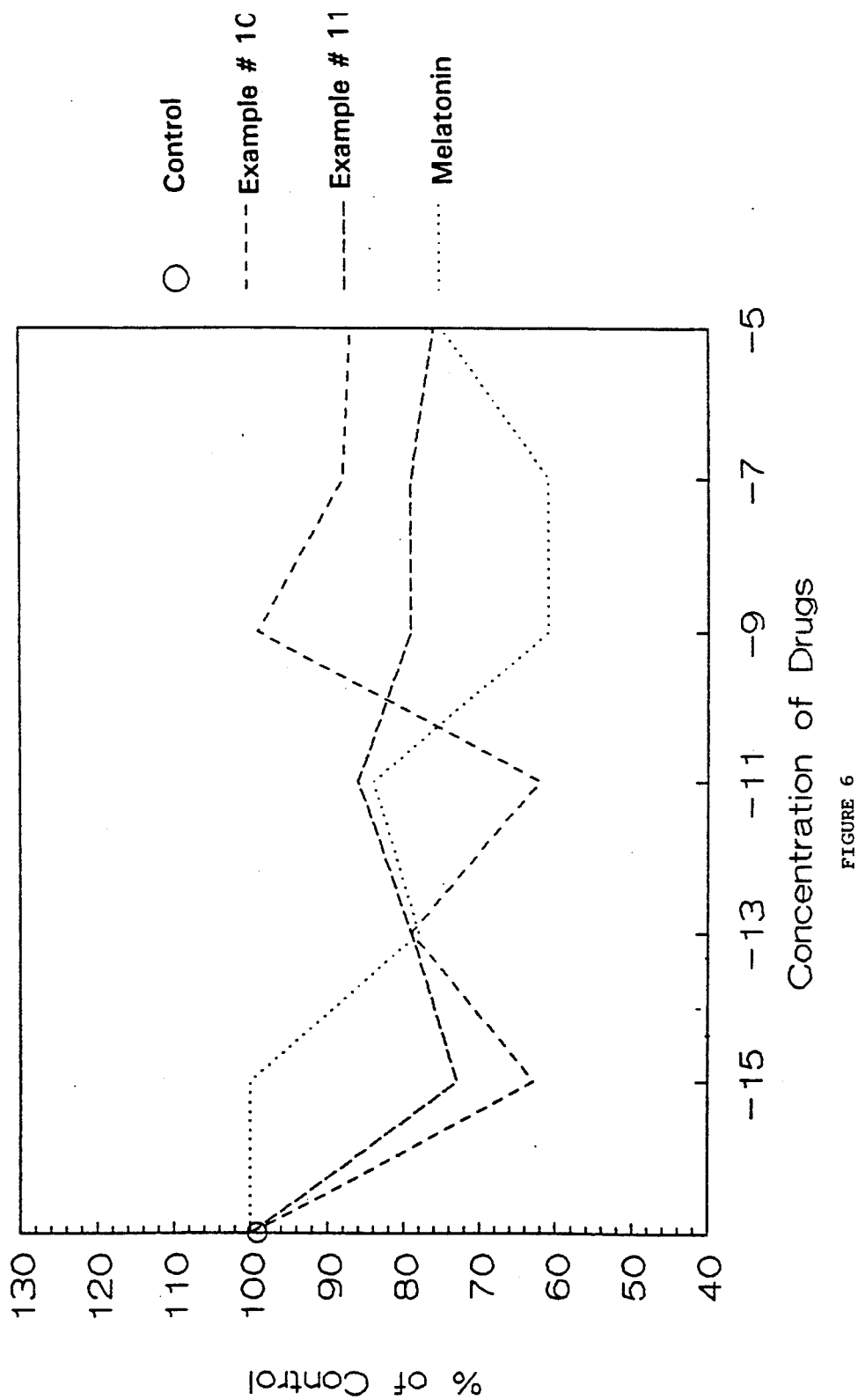

FIG. 6 shows that Example #10 inhibits MCF-7 cell growth at $10^{-15}M, 10^{-13}M$, and $10^{-11}M$, showing an $IC_{50}$ of $1 \times 10^{-16}M$. Example #11 inhibits MCF-7 cell growth at $10^{-15}M$ and $10^{-13}M$, with an $IC_{50}$ of $2 \times 10^{-16}M$.

Figure 7:
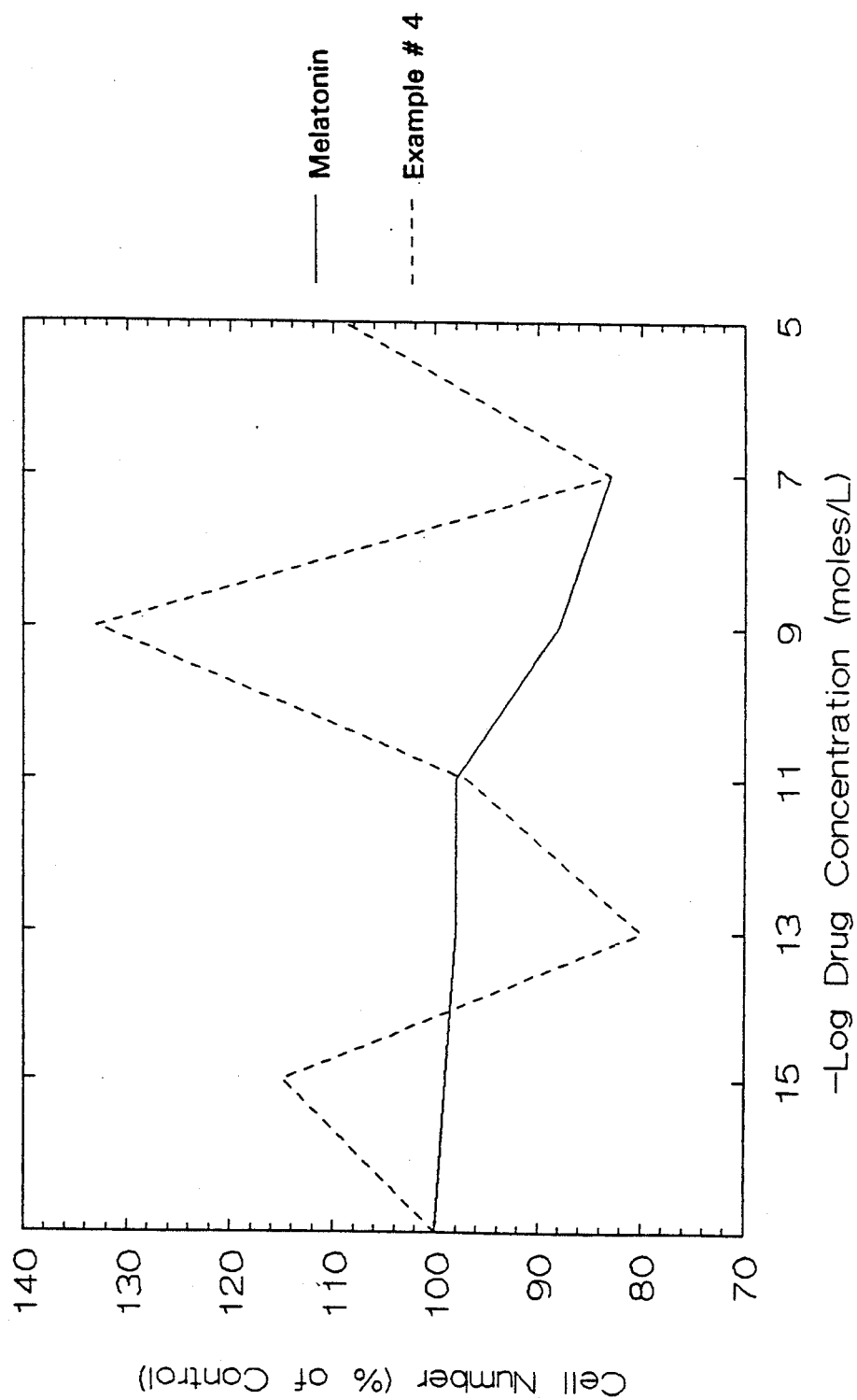
FIGS. 7-15 describe effects of compounds on cell growth described in Examples 4, 7 and 3, 2, 8, 1, 5, 11, 10, as well as 9.

Continuing with results in the estrogen negative cell line, FIG. 7 shows Example #4 inhibits Hs0578t cell growth at $10^{-13}M$ and $10^{-7}M$, With an $IC_{50}$ of $1 \times 10^{-15}M$.

Figure 8:
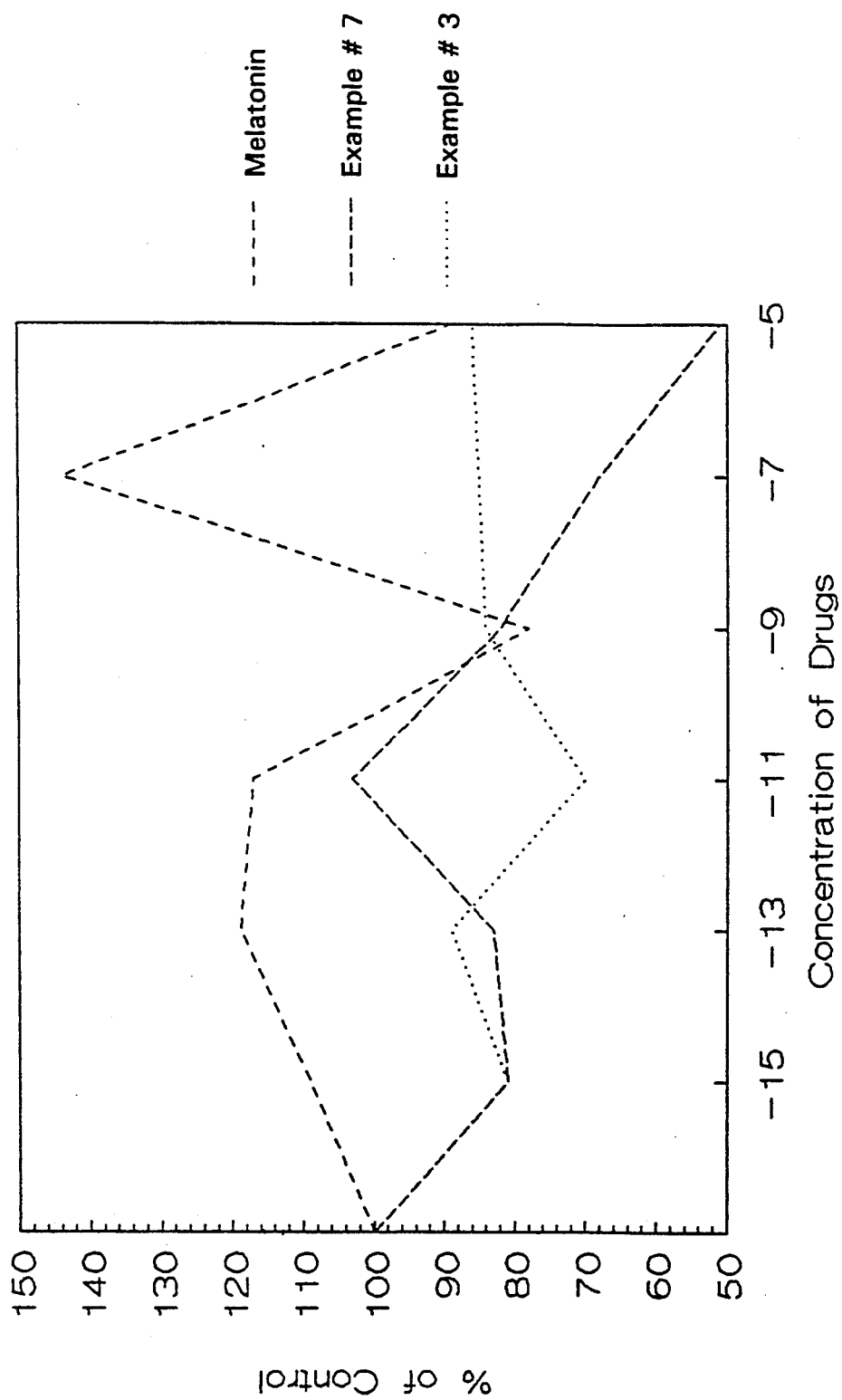
Figure 9:
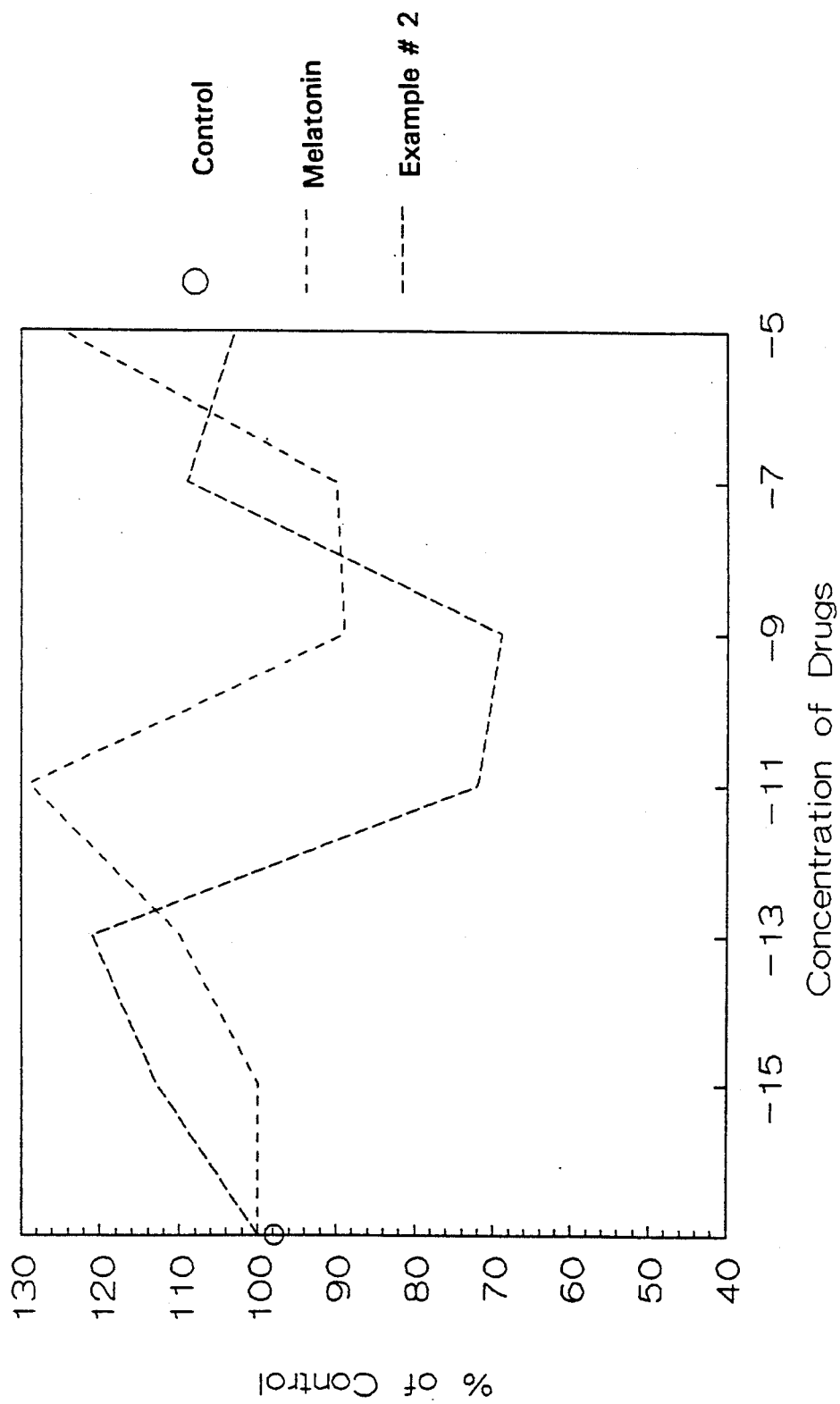

The effects of Examples #7 and 3 on Hs0578t cell growth are summarized in FIG. 8. All concentrations of these compounds were inhibitory to cell growth, with the exception of Example #7 at $10^{-11}M$. The $IC_{50}$ of Example #7 is about $1 \times 10^{-8}M$, while the $IC_{50}$ of Example #3 is $1 \times 10^{-13}M$, FIG. 9 shows Example #2 inhibits Hs0578t cell growth at $10^{-11}M$ and $10^{-9}M$, With an $IC_{50}$ of approximately $8 \times 10^{-13}M$.

Figure 10:
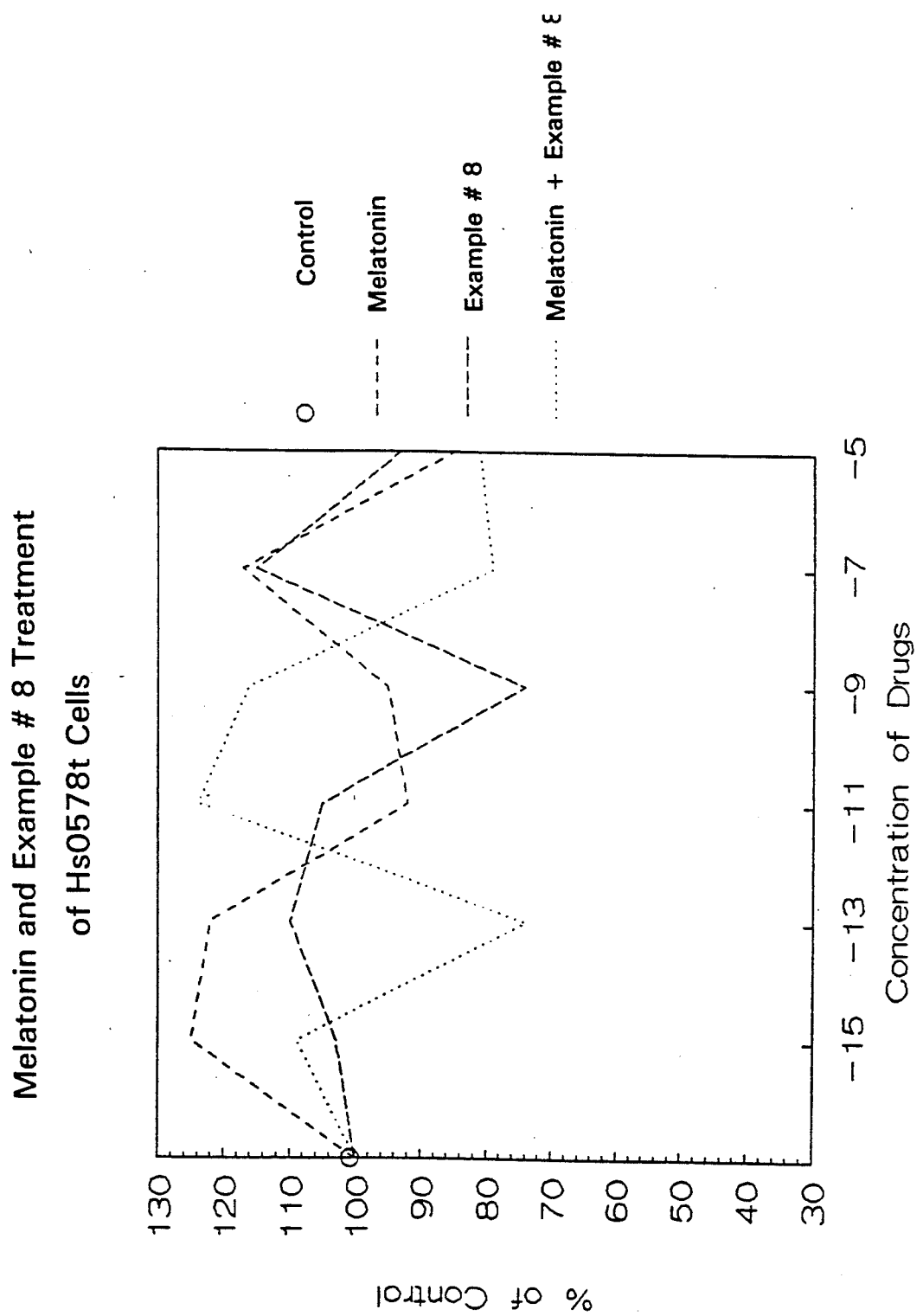
Figure 11:
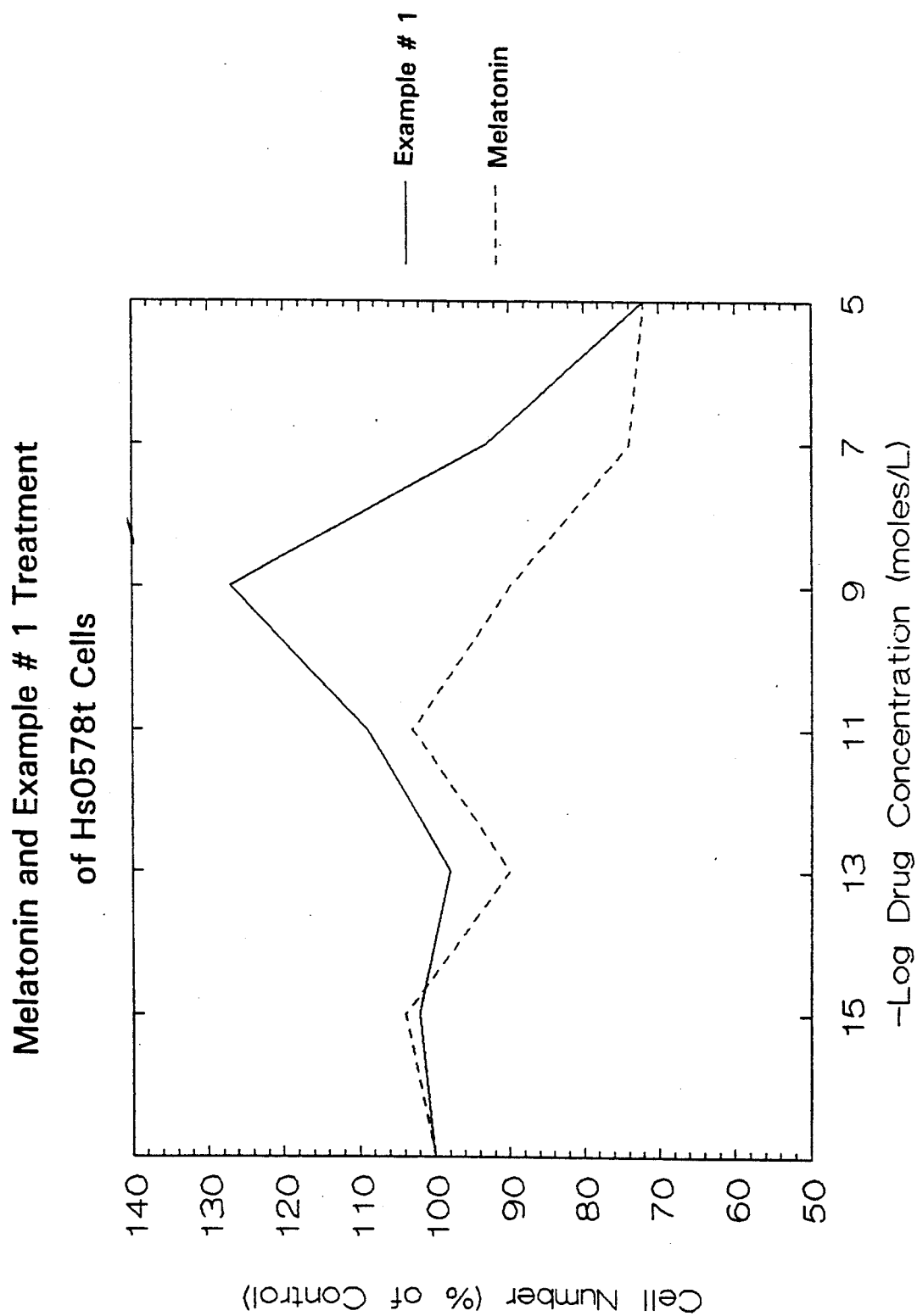

FIG. 10 shows Example #8 inhibits Hs0578t cell growth at $10^{-9}M$ with an $IC_{50}$ of approximately $1 \times 10^{-10}M$.

Figure 12:
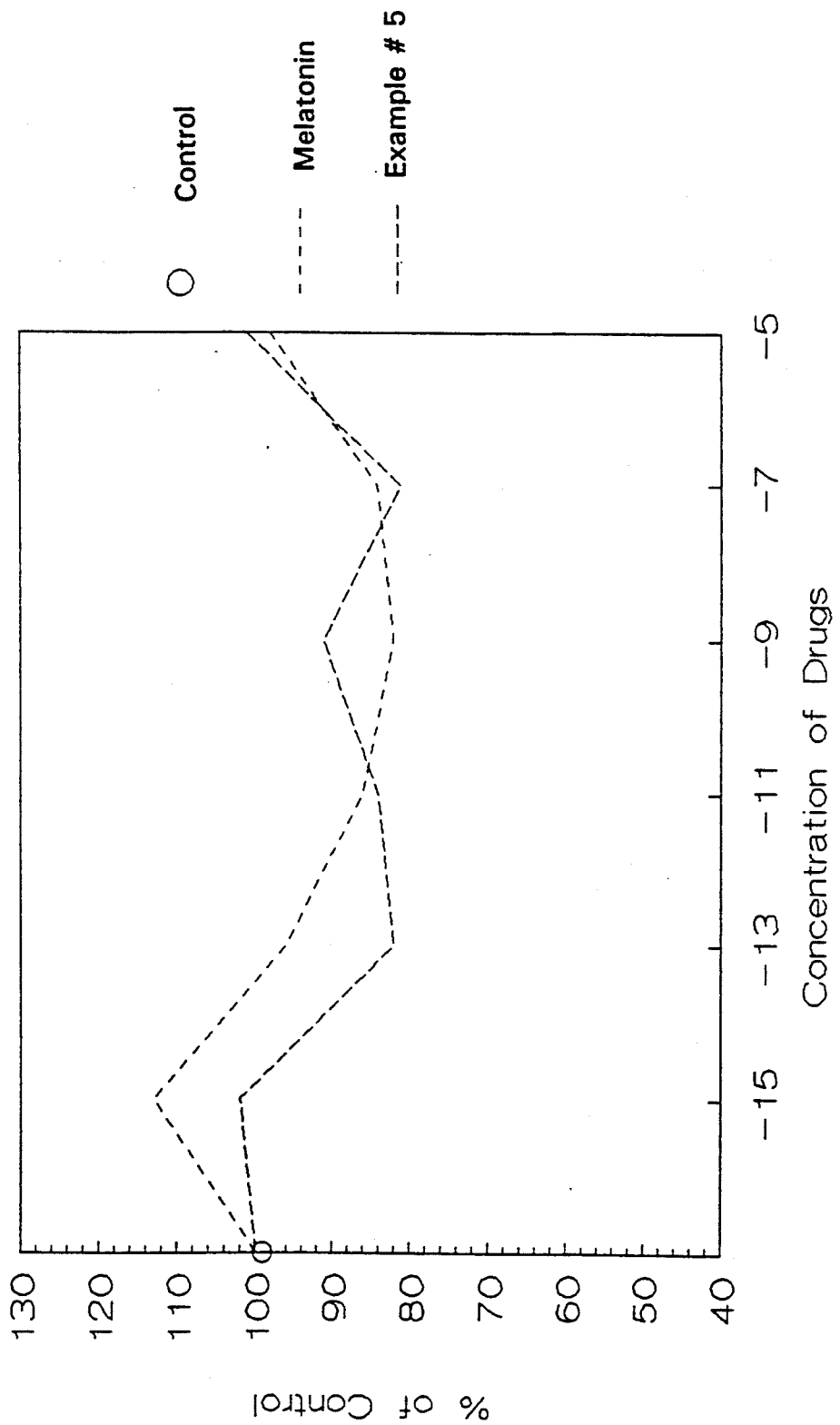
Figure 13:
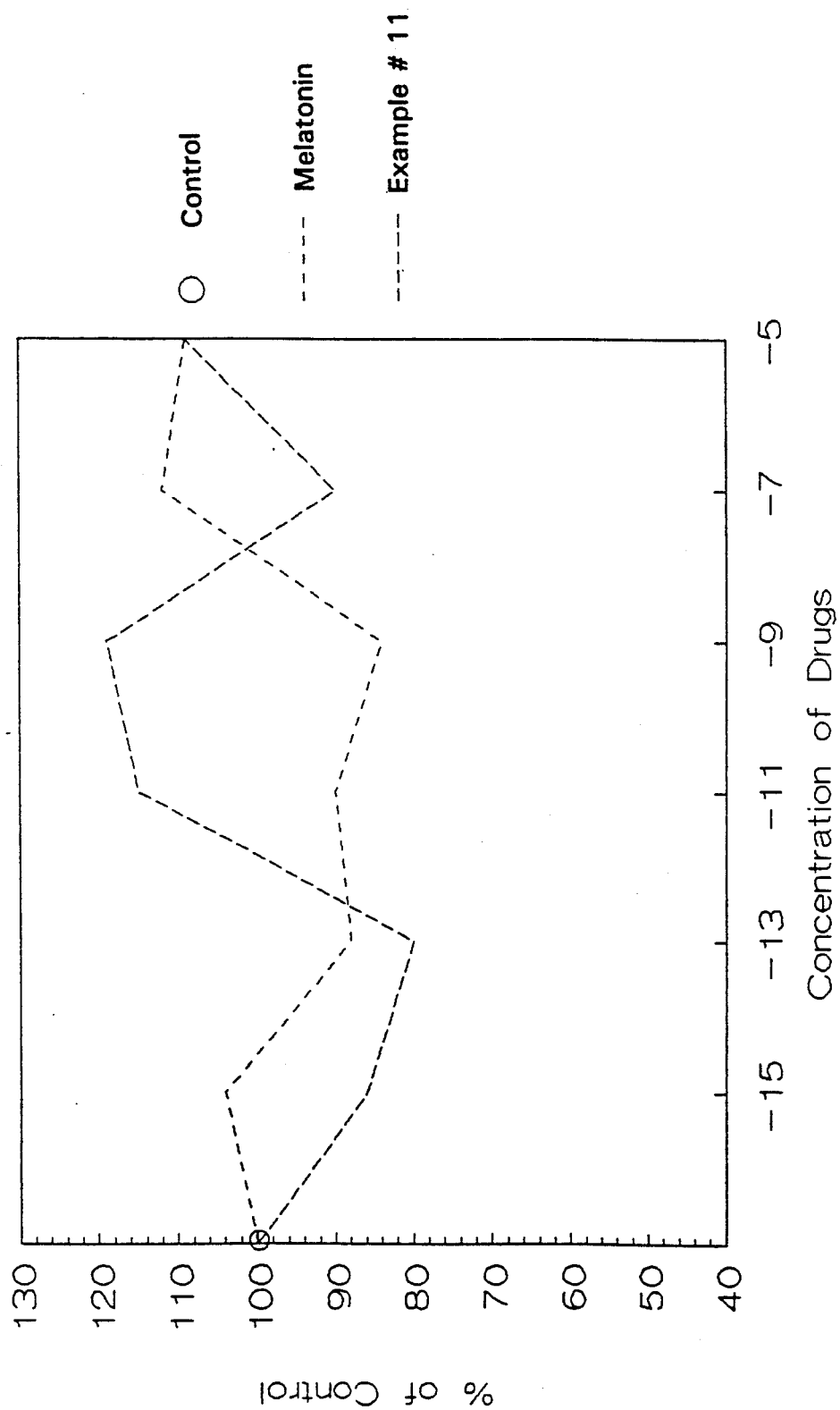
Figure 14:
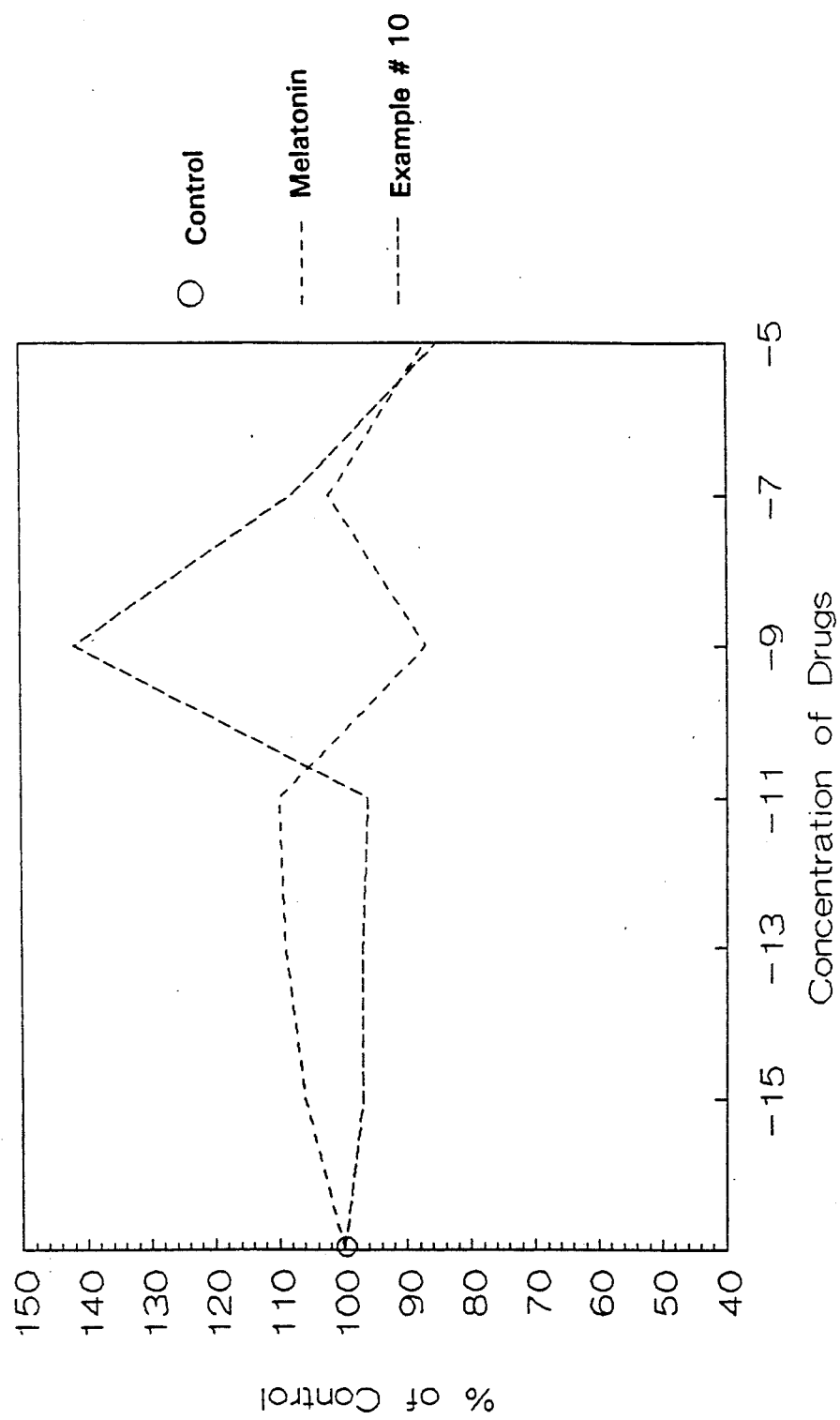

Example #1 (FIG. 11) shows inhibition of Hs0578t cell growth only at $10^{-5}M$, while cell growth is actually stimulated at $10^{-9}M$, resulting in an $IC_{50}$ of approximately $6 \times 10^{-9}M$ FIGS. 12–14 show no inhibition of Hs0578t cell growth was observed for Examples #5, 11, and 10.

Figure 15:
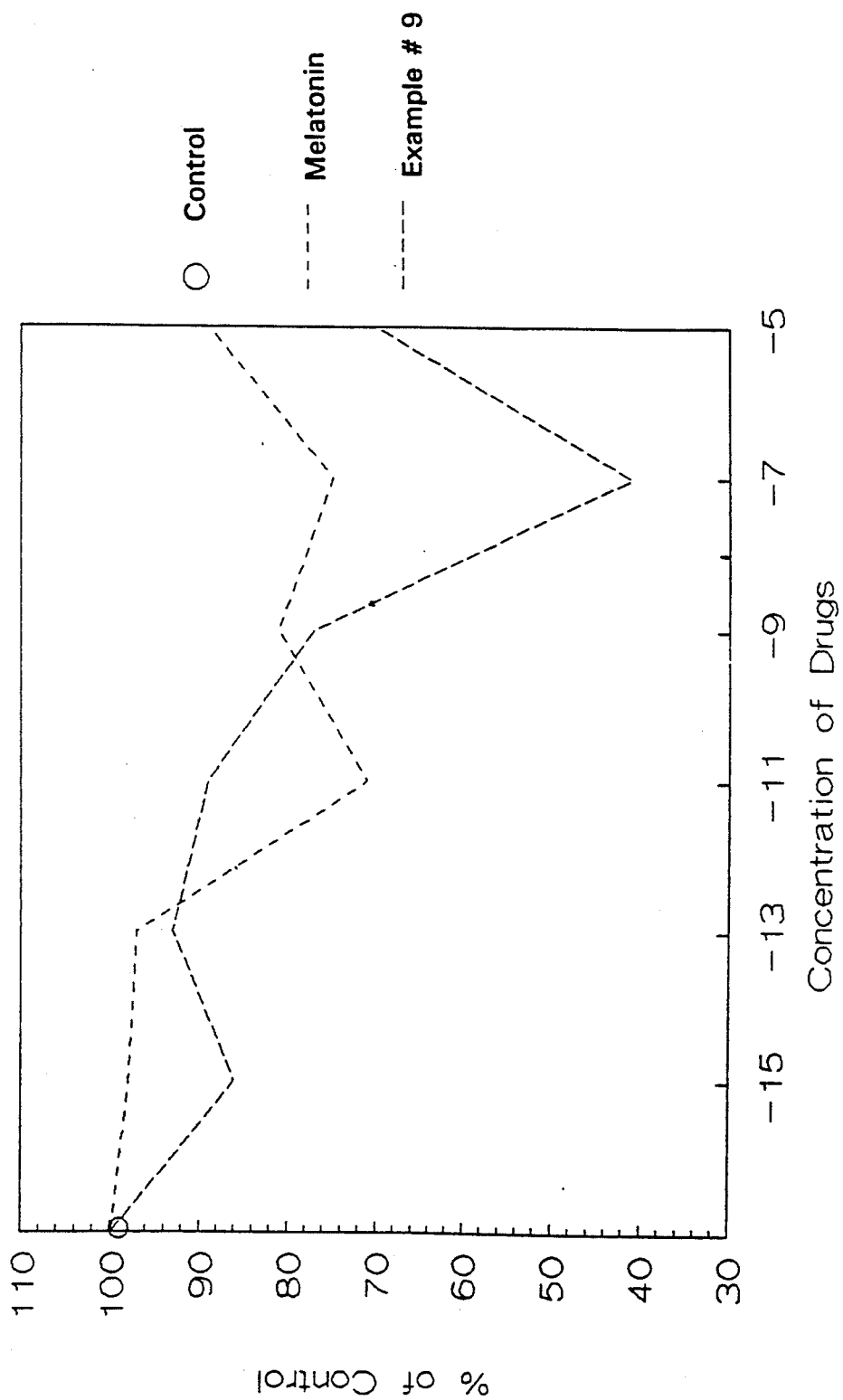

FIG. 15 shows Example #9 inhibits Hs0578t cell growth at $10^{-5}M$ and $10^{-7}M$, with an $IC_{50}$ of approximately $4 \times 10^{-9}M$.

It is clear from the above data that all examples exhibited some degree of inhibition of the estrogen positive human breast cancer cell line MCF-7. While the dose-response curves were complex, all the examples tested show IC50's in the $10^{-15}M$ to $10^{-16}M$ range, indicating that these analogues are remarkably potent inhibitors of estrogen positive human cancer cell growth. In comparison to melatonin, which yielded IC50's in the $10^{-14}M$ to $10^{-10}M$ concentration range, the above examples are from 60 to one million times more potent inhibitors of MCF-7 cell growth.

In the estrogen negative cell line tested (Hs0578t), seven out of ten examples exhibited some degree of inhibition of cell growth. Melatonin, tested in this cell line, had no inhibitory effect in most experiments. A wide range of IC$_{50}$'s was seen ($10^{-15}$M to $10^{-7}$M).

Example #6 appears to be the most potent inhibitor of MCF-7 cell growth, while Example #2 elicits the best maximal inhibitory response. Example #4 appears to be the most potent inhibitor of Hs0578t cells, while Example #9 shows the best maximal inhibition of growth. Example #11 is not only a highly potent compound, but it elicits an impressive maximal inhibitory response at a very low concentration. Example #2 is not only a highly potent inhibitor of both cell lines, but also induces in both a substantial inhibitory response at low concentrations.

Having now described the invention, I claim:

1. Compounds of the formula

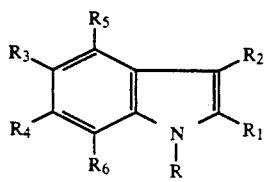

where R is hydrogen or C$_1$ to C$_6$ linear or branched alkylene substituted with phenyl;

R$_1$ is benzyl, or naphthylmethyl;

R$_2$ is the group —(CH$_2$)$_m$—NHR$_2'$, where m is 1 to 3 and R$_2'$ is phenyl sulfonyl, the phenyl group optionally substituted with alkyl, or —C(O)—R$_2''$, where R$_2''$ is C$_1$ to C$_6$ linear or branched alkylene substituted with a substituent selected from the group consisting of hydrogen, phenyl, alkoxy, alkoxy substituted with phenyl, carboxylic acid or the alkyl esters thereof, carbamoyloxy alkyl, carbamoyloxy alkyl substituted with phenyl or phenyl substituted with at least one substituent selected from the group consisting halo, amino, nitro, hydroxy, alkyl, alkoxy, and haloalkyl, and amino or 5-(2-alkanoyl) tetrazole;

R$_3$, R$_4$, R$_5$ and R$_6$ are the same or different and are hydrogen, C$_1$ to C$_6$ linear or branched alkyl, C$_1$ to C$_6$ linear or branched alkoxy, phenoxy or phenoxy substituted with one or more C$_1$ to C$_6$ linear or branched alkyl.

2. The compounds according to claim 1 wherein R, R$_3$, R$_4$, R$_5$ and R$_6$ are hydrogen and R$_2$ is the group —(CH$_2$)$_m$—NHR$_2'$ where m is 1 to 3 and R$_2'$ is —C(O)—R$_2''$ where R$_2''$ is C$_1$ to C$_6$ linear or branched alkylene substituted with a substituent selected from the group consisting of phenyl, C$_1$ to C$_6$ linear or branched alkoxy optionally substituted with phenyl, carboxyl and or the C$_1$ to C$_6$ linear or branched alkyl esters thereof, carbamoyloxy alkyl and amino.

3. The compounds according to claim 1 wherein R$_2''$ is C$_1$ to C$_6$ linear or branched alkylene substituted with C$_1$ to C$_6$ linear or branched alkoxy optionally substituted with phenyl.

4. The compounds according to claim 3 wherein said alkoxy is ethoxy.

5. The compounds according to claim 3 wherein said alkoxy is methoxy substituted with phenyl.

6. The compounds according to claim 2 wherein R$_2''$ is C$_1$ to C$_6$ linear or branched alkylene substituted with carboxylic acid and the C$_1$ to C$_6$ linear or branched alkyl esters thereof.

7. The compounds according to claim 2 wherein R$_2''$ is C$_1$ to C$_6$ linear or branched alkylene substituted with carbamoyloxy C$_1$ to C$_6$ alkyl optionally substituted with phenyl.

8. The compounds according to claim 7 wherein said carbamoyloxy C$_1$ to C$_6$ linear or branched alkyl is carbamoyloxymethyl substituted with phenyl.

* * * * *